United States Patent [19]

Regel et al.

[11] 3,985,766

[45] Oct. 12, 1976

[54] BIS-IMIDAZOLYL-BISPHENYLMETHANE AND SALTS THEREOF

[75] Inventors: Erik Regel, Wuppertal; Karl Heinz Buchel; Manfred Plempel, both of Wuppertal-Elberfeld, all of Germany

[73] Assignee: Bayer Aktiengesellschaft, Germany

[22] Filed: Oct. 31, 1969

[21] Appl. No.: 873,098

[30] Foreign Application Priority Data
Nov. 5, 1968  Germany............................ 1806995

[52] U.S. Cl.............................. 260/309; 260/465 G; 260/607 A; 260/609 R; 260/612 D; 260/646; 260/649 F; 260/649 DP; 424/273
[51] Int. Cl.² ....................................... C07D 233/56
[58] Field of Search .................................... 260/309

[56] References Cited
UNITED STATES PATENTS

| 3,073,841 | 1/1963 | Schindler............................ 260/309 |
| 3,321,366 | 5/1967 | Mussell et al........................ 260/309 |

OTHER PUBLICATIONS

Tolkkmith et al., Science vol. 158, pp. 1462–1463, (1967).
Fournari et al., Bul. Soc. Chim. France 1968, pp. 2438–2446, (1968, June 1968).

*Primary Examiner*—Natalie Trousof

[57] ABSTRACT

Bis-imidazolyl-bisphenylmethane derivatives and pharmaceutically acceptable non-toxic salts thereof are useful as antimycotics especially against dermatomycosis caused by *Trichophyton* and *Microsporium* species and also against yeast infections of the skin and internal organs.

11 Claims, No Drawings

BIS-IMIDAZOLYL-BISPHENYLMETHANE AND SALTS THEREOF

The present invention is concerned with bis-imidazolyl-bisphenylmethanes, salts thereof, processes for their production, pharmaceutical compositions containing such compounds and methods of treating fungal infections pathogenic to humans and animals and methods of treating yeast infections pathogenic to humans and animals. More particularly, the compounds of the present invention are bis-imidazolyl-bisphenylmethanes which may be substituted in one or both of the imidazolyl moieties and one or both of the phenyl moieties.

The compounds of the present invention are particularly useful as antimycotics especially against dermatomycosis caused by Trichophyton and Microsporium species and also against yeast infections of the skin and internal organs.

The compounds of the present invention may be represented by the formula:

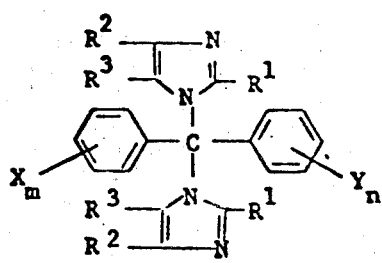

wherein
$R^1$ is hydrogen, alkyl, aryl or substituted aryl,
$R^2$ and $R^3$ are the same or different and are hydrogen, alkyl, aryl, substituted aryl, or $R^2$ and $R^3$ together form a fused benzene ring,
X and Y are the same or different and are an electronegative moiety, alkyl, S-alkyl or alkoxy,
$m$ is 0, 1 or 2,
$n$ is 0, 1 or 2,
and includes salts of such compounds.

When $R^1$, $R^2$ and $R^3$ is alkyl, it is preferred that the alkyl moiety contain from 1 to 4 carbon atoms. When it is aryl, it is preferred that the aryl moiety contain up to 10 carbon atoms in the ring system and the preferred aryl moiety is phenyl. The aryl may be substituted in which event the preferred substituents are lower alkyl, S-alkyl or alkoxy, haloalkyl of 1 to 4 carbon atoms in the alkyl portion and preferably 1 or 2 carbon atoms in the alkyl portion and wherein the halogen is preferably fluorine, chlorine or bromine, or by an electronegative moiety, preferably a halogen.

When X or Y is alkyl, it is preferred that the alkyl moiety contain from 1 to 12 carbon atoms and preferably 1 to 4 carbon atoms. When it is S-alkyl or alkoxy, it is preferred that the alkyl portions contain from 1 to 4 carbon atoms. When it is an electronegative moiety, it is preferred that the electronegative moiety be halogen, i.e. fluorine, chlorine, bromine or iodine, $NO_2$, $CF_3$ or CN.

It is to be appreciated that when X or Y is more than one such moiety as above defined, such as in the case where $m$ or $n$ is 2, that the moieties may be the same or different.

The term alkyl includes straight chain and branched chain alkyl moieties as well as the saturated alkyl moieties and the partially unsaturated moieties, i.e. those containing a double bond.

The salts of the bis-imidazolyl-bisphenylmethanes of the present invention are preferably pharmaceutically acceptable non-toxic salts and examples of acids which give salts useful as hereinabove discussed include the halogen hydracids, phosphoric acids, mono- and bifunctional carboxylic acids and hydroxycarboxylic acids, for example, acetic acid, propionic acid, maleic acid, succinic acid, fumaric acid, tartaric acid, citric acid, salicylic acid, sorbic acid and lactic acid and 1,5-naphthalene-di-sulphonic acid. Of particular interest are the hydrohalides, particularly the chlorides, lactates and salicylates of the bis-imidazolyl-bisphenylmethanes.

According to a preferred embodiment of the present invention, $R^1$, $R^2$ and $R^3$ are hydrogen, X and Y are the same or different and are fluorine, chlorine, bromine, iodine, CN, $NO_2$, methoxy, thiomethyl or $CF_3$ and $m$ and $n$ are 1.

The bis-imidazolyl-bisphenylmethanes of the present invention may be produced by reacting a diphenyl-dihalomethane of the formula:

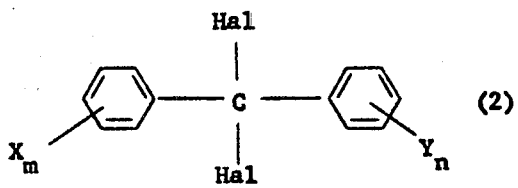

wherein X, Y, $m$ and $n$ are as above defined and wherein Hal is chlorine, bromine or iodine, with the stoichiometric amount of an imidazole derivative of the formula:

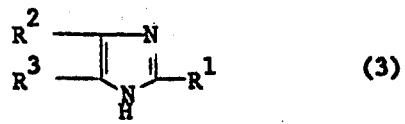

wherein $R^1$, $R^2$ and $R^3$ are as above defined, in the presence of an inert polar solvent and of the stoichiometric amount of an acid acceptor, at a temperature range of from about 0° C to about 100° C. It is preferred that the reaction temperature be in the range of 50° C to 80° C.

Examples of suitable solvents are ketones, such as acetone, methyl ethyl ketone, diethyl ketone and as examples representing other types of solvents, dimethyl formamide, acetonitrile and nitromethane.

As acid acceptor two further equivalents of the imidazole derivative may be used: however, the corresponding quantity of one of the conventional tertiary amines is preferably used, such as triethylamine, dimethylanilin, N,N-dimethyl-benzylamine and the like.

The starting materials used for the process of the present invention, i.e. the diphenyl-dihalomethanes of the formula: (2) and the imidazole derivatives of the formula (3) are known or can be obtained according to methods and/or procedures per se known.

The following examples are representative of compounds of the formula (2):

Diphenyldichloromethane
2-fluoro-diphenyldichloromethane
3-fluoro-diphenyldichloromethane
4-fluoro-diphenyldichloromethane
2-chloro-diphenyldichloromethane
3-chloro-diphenyldichloromethane
4-chloro-diphenyldichloromethane
2-bromo-diphenyldichloromethane
3-bromo-diphenyldichloromethane
4-bromo-diphenyldichloromethane
2-nitro-diphenyldichloromethane
3-nitro-diphenyldichloromethane
4-nitro-diphenyldichloromethane
2-cyano-diphenyldichloromethane
3-cyano-diphenyldichloromethane
4-cyano-diphenyldichloromethane
2-methyl-diphenyldichloromethane
3-methyl-diphenyldichloromethane
4-methyl-diphenyldichloromethane
2-ethyl-diphenyldichloromethane
3-ethyl-diphenyldichloromethane
4-ethyl-diphenyldichloromethane
2-methoxy-diphenyldichloromethane
3-methoxy-diphenyldichloromethane
4-methoxy-diphenyldichloromethane
2-methyl-thio-diphenyldichloromethane
3-methyl-thio-diphenyldichloromethane
4-methyl-thio-diphenyldichloromethane
2-methyl-sulphinyl-diphenyldichloromethane
3-methyl-sulphinyl-diphenyldichloromethane
4-methyl-sulphinyl-diphenyldichloromethane
2-methyl-sulphonyl-diphenyldichloromethane
3-methyl-sulphonyl-diphenyldichloromethane
4-methyl-sulphonyl-diphenyldichloromethane
4-tert.butyldiphenyldichloromethane
4-phenyl-diphenyldichloromethane
2,4-dichloro-diphenyldichloromethane
2,5-dichloro-diphenyldichloromethane
3,4-dichloro-diphenyldichloromethane
4-chloro-2-nitro-diphenyldichloromethane
4-chloro-3-nitro-diphenyldichloromethane
6-chloro-3-nitro-diphenyldichloromethane
2-chloro-4-nitro-diphenyldichloromethane
2,4-dinitro-diphenyldichloromethane
3,4-dinitro-diphenyldichloromethane
3,5-dinitro-diphenyldichloromethane
4-nitro-3-methyl-diphenyldichloromethane
3-nitro-4-methyl-diphenyldichloromethane
2,2'-difluoro-diphenyldichloromethane
2,3'-difluoro-diphenyldichloromethane
2,4'-difluoro-diphenyldichloromethane
3,3'-difluoro-diphenyldichloromethane
3,4'-difluoro-diphenyldichloromethane
4,4'-difluoro-diphenyldichloromethane
2-fluoro-2'-chloro-diphenyldichloromethane
2-fluoro-3'-chloro-diphenyldichloromethane
2-fluoro-4'-chloro-diphenyldichloromethane
3-fluoro-3'-chloro-diphenyldichloromethane
3-fluoro-4'-chloro-diphenyldichloromethane
4-fluoro-4'-chloro-diphenyldichloromethane
4-fluoro-4'-bromo-diphenyldichloromethane
2,2'-dichloro-diphenyldichloromethane
2,3'-dichloro-diphenyldichloromethane
2,4'-dichloro-diphenyldichloromethane
3,3'-dichloro-diphenyldichloromethane
3,4'-dichloro-diphenyldichloromethane
4,4'-dichloro-diphenyldichloromethane
2-chloro-4'-bromo-diphenyldichloromethane
3-chloro-4'-bromo-diphenyldichloromethane
4-chloro-4'-bromo-diphenyldichloromethane
4-fluoro-2'-nitro-diphenyldichloromethane
4-fluoro-3'-nitro-diphenyldichloromethane
4-fluoro-4'-nitro-diphenyldichloromethane
4-chloro-2'-nitro-diphenyldichloromethane
4-chloro-3'-nitro-diphenyldichloromethane
4-chloro-4'-nitro-diphenyldichloromethane
4-bromo-2'-nitro-diphenyldichloromethane
4-bromo-3'-nitro-diphenyldichloromethane
4-bromo-4'-nitro-diphenyldichloromethane
4-fluoro-4'-cyano-diphenyldichloromethane
4-chloro-4'-cyano-diphenyldichloromethane
4-bromo-4'-cyano-diphenyldichloromethane
2-methyl-2'-fluoro-diphenyldichloromethane
2-methyl-3'-fluoro-diphenyldichloromethane
2-methyl-4'-fluoro-diphenyldichloromethane
2-methyl-2'-chloro-diphenyldichloromethane
2-methyl-3'-chloro-diphenyldichloromethane
2-methyl-4'-chloro-diphenyldichloromethane
3-methyl-2'-fluoro-diphenyldichloromethane
3-methyl-3'-fluoro-diphenyldichloromethane
3-methyl-4'-fluoro-diphenyldichloromethane
3-methyl-2'-chloro-diphenyldichloromethane
3-methyl-3'-chloro-diphenyldichloromethane
3-methyl-4'-chloro-diphenyldichloromethane
4-methyl-2'-chloro-diphenyldichloromethane
4-methyl-3'-chloro-diphenyldichloromethane
4-methyl-4'-chloro-diphenyldichloromethane
4-tert.-butyl-2'-fluoro-diphenyldichloromethane
4-tert.-butyl-3'-fluoro-diphenyldichloromethane
4-tert.-butyl-4'-fluoro-diphenyldichloromethane
4-tert.-butyl-2'-chloro-diphenyldichloromethane
4-tert.-butyl-3'-chloro-diphenyldichloromethane
4-tert.-butyl-4'-chloro-diphenyldichloromethane
2,4-dichloro-2'-fluoro-diphenyldichloromethane
2,4-dichloro-3'-fluoro-diphenyldichloromethane
2,4-dichloro-4'-fluoro-diphenyldichloromethane
2,4-dichloro-2'-chloro-diphenyldichloromethane
2,4-dichloro-3'-chloro-diphenyldichloromethane
2,4-dichloro-4'-chloro-diphenyldichloromethane
2,5-dichloro-2'-fluoro-diphenyldichloromethane
2,5-dichloro-3'-fluoro-diphenyldichloromethane
2,5-dichloro-4'-fluoro-diphenyldichloromethane
2,5-dichloro-2'-chloro-diphenyldichloromethane
2,5-dichloro-3'-chloro-diphenyldichloromethane
2,5-dichloro-4'-chloro-diphenyldichloromethane
3,4-dichloro-2'-fluoro-diphenyldichloromethane
3,4-dichloro-3'-fluoro-diphenyldichloromethane
3,4-dichloro-4'-fluoro-diphenyldichloromethane
3,4-dichloro-2'-chloro-diphenyldichloromethane
3,4-dichloro-3'-chloro-diphenyldichloromethane
3,4-dichloro-4'-chloro-diphenyldichloromethane
4-chloro-2'-fluoro-2-nitro-diphenyldichloromethane
4-chloro-3'-fluoro-2-nitro-diphenyldichloromethane
4-chloro-4'-fluoro-2-nitro-diphenyldichloromethane
4-chloro-2'-chloro-2-nitro-diphenyldichloromethane
4-chloro-3'-chloro-2-nitro-diphenyldichloromethane
4-chloro-4'-chloro-2-nitro-diphenyldichloromethane
4-chloro-2'-fluoro-3-nitro-diphenyldichloromethane
4-chloro-3'-fluoro-3-nitro-diphenyldichloromethane
4-chloro-4'-fluoro-3-nitro-diphenyldichloromethane
4-chloro-2'-chloro-3-nitro-diphenyldichloromethane
4-chloro-3'-chloro-3-nitro-diphenyldichloromethane
4-chloro-4'-chloro-3-nitro-diphenyldichloromethane
6-chloro-4'-fluoro-3-nitro-diphenyldichloromethane
6-chloro-4'-chloro-3-nitro-diphenyldichloromethane
2-chloro-4'-chloro-4-nitro-diphenyldichloromethane 2-chloro-4'-fluoro-4-nitro-diphenyldichloromethane
4-chloro-2',4'-dinitro-diphenyldichloromethane
4-chloro-3',4'-dinitro-diphenyldichloromethane
4-chloro-3',5'-dinitro-diphenyldichloromethane
4-chloro-3'-methyl-4'-nitro-diphenyldichloromethane
4-chloro-4'-methyl-3'-nitro-diphenyldichloromethane
2,2',5,5'-tetrachloro-diphenyldichloromethane
2-fluoro-4'-methoxy-diphenyldichloromethane
3-fluoro-4'-methoxy-diphenyldichloromethane
4-fluoro-4'-methoxy-diphenyldichloromethane
2-chloro-4'-methoxy-diphenyldichloromethane
3-chloro-4'-methoxy-diphenyldichloromethane
4-chloro-4'-methoxy-diphenyldichloromethane
2-methyl-4'-methoxy-diphenyldichloromethane
3-methyl-4'-methoxy-diphenyldichloromethane
4-methyl-4'-methoxy-diphenyldichloromethane
2-fluoro-4'-methylthio-diphenyldichloromethane
3-fluoro-4'-methylthio-diphenyldichloromethane
4-fluoro-4'-methylthio-diphenyldichloromethane
2-chloro-4'-methylthio-diphenyldichloromethane
3-chloro-4'-methylthio-diphenyldichloromethane
4-chloro-4'-methylthio-diphenyldichloromethane
2,4-dichloro-4'-methylthio-diphenyldichloromethane
2,5-dichloro-4'-methylthio-diphenyldichloromethane
3,4-dichloro-4'-methylthio-diphenyldichloromethane
2,4-dichloro-4'-methoxy-diphenyldichloromethane
2,5-dichloro-4'-methoxy-diphenyldichloromethane
3,4-dichloro-4'-methoxy-diphenyldichloromethane
4-ethylthio-2-chloro-diphenyldichloromethane
4-ethylsulphonyl-2-chloro-diphenyldichloromethane The following examples are representative of compounds of the formula (3);
imidazole
2-methylimidazole
2-ethylimidazole
2-phenylimidazole
4,(5)-phenylimidazole
4,5-diphenylimidazole
benzimidazole Salts of compounds of the formula (1) may be converted into their corresponding salts by techniques per se known. For example, 0.2 mol of a bis-imidazolyl-bis-phenylmethane may be dissolved with heating in acetonitrile, followed by the addition of 0.22 ml D,L-lactic acid. The residue remaining after the solvent has been distilled off may be made to crystallize by covering it, after filtration, with a layer of ether; the crystalline product may be washed with ether and dried.

The hydrochlorides are expediently obtained by introducing hydrogen chloride into the solution of the imidazole derivative, for example, in carbon tetrachloride.

The following table shows examples of the compounds of the invention:

| | | m.p.° C |
|---|---|---|
| a) | bis-imidazolyl-bis-phenylmethane | 190 |
| b) | bis-imidazolyl-4-chlorophenyl-phenylmethane | 140 |
| c) | bis-imidazolyl-4-fluorophenyl-phenylmethane | 130 |
| d) | bis-imidazolyl-2,4'-difluoro-diphenylmethane | 129 |
| e) | bis-imidazolyl-2-chlorophenyl-phenylmethane | 143 |
| f) | bis-imidazolyl-3-chlorophenyl-phenylmethane | 118 |
| g) | bis-imidazolyl-4-cyanophenyl-phenylmethane | 125 |
| h) | bis-(2-methylimidazolyl)-4-chlorophenyl-phenylmethane | 215 |

-continued

| | m.p.° C |
|---|---|
| phenylmethane | 215 |

The compounds and salts of the formula (1) can be used, inter alia, in the form of an aqueous emulsion, suspension or solution. It is also possible to use the aqueous solutions of the salts of the above compounds.

The invention is illustrated by the following Examples.

EXAMPLE 1

Bis-imidazolyl-4-chlorophenyl-phenylmethane

To a solution of 27.2 g (0.4 mol) imidazole and 40.4 g (0.4 mol) triethylamine in 300 ml acetonitrile there are added dropwise 54 g (0.2 mol) 4-chlorophenyl-phenyl-dichloromethane. The triethylamine hydrochloride formed starts to separate at room temperature. The mixture is heated at 80° C for 12 hours to complete the reaction. After cooling, the reaction mixture is stirred with 500 ml benzene and washed with water until free of salt. The benzene solution is dried over anhydrous sodium sulphate, filtered and concentrated by evaporation; after recrystallisation of the crude product from acetonitrile, there result 41 g of pure bis-imidazolyl-4-chlorophenyl-phenylmethane of m.p. 140° C.

| $C_{19}H_{15}ClN_4$ | mol. weight 334.5 | | | | | | |
|---|---|---|---|---|---|---|---|
| calculated: | C | 68.0% | H | 4.5% | Cl | 10.6% | N | 16.7% |
| Found: | C | 68.0% | H | 4.8% | Cl | 10.7% | N | 16.9% |

The same compound is obtained when, as starting compound, the dichloromethane compound is replaced by 4-chlorophenyl-phenyl-dibromomethane or the corresponding diiodine compound.

EXAMPLE 2

Bis-imidazolyl-4-fluorophenyl-phenylmethane

Into a solution of 29.4 g (0.43 mol) imidazole and 43.7 g (0.43 mol) triethylamine in 300 ml acetonitrile there are added dropwise 55 g (0.21 mol) 4-fluorophenyl-phenyl-dichloromethane. Separation of the triethylammonium chloride formed begins at room temperature. The mixture is heated at 80° C for 12 hours to complete the reaction. After cooling, the reaction mixture is stirred with 500 ml benzene and washed with water until free of salt. The benzene solution is dried over anhydrous sodium sulphate, filtered and evaporated; after recrystallisation of the crude product from acetonitrile there result 42 g pure bis-imidazolyl-4-fluorophenyl-phenyl-methane of m.p. 130° C.

| $C_{19}H_{15}FN_4$ | mol. weight 318 | | | | | | |
|---|---|---|---|---|---|---|---|
| calculated: | C | 71.8% | H | 4.7% | F | 6.0% | N | 17.6% |
| found: | C | 71.7% | H | 4.9% | F | 6.0% | N | 17.6% |

The following compounds of the formula (4) are prepared in a manner analogous to that set forth in Example 2 by reacting the appropriate diphenyl-dichloromethane from the list on pages 5 to 10 with the appropriate imidazole set forth on page 11.

EXAMPLES 3 – 9

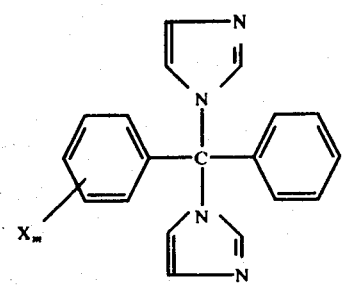

(4)

| | X | m.p. °C |
|---|---|---|
| 3 | H | 190 |
| 4 | 2-Cl | 143 |
| 5 | 3-Cl | 118 |
| 6 | 4-CN | 125 |
| 7 | 4-Br | 137 |
| 8 | 4-$NO_2$ | 163 |
| 8a | 4-$CH_3O$ | 122 |
| 8b | 3-$NO_2$, 4-Cl | 207 |
| 8c | 3-$NO_2$, 4-$CH_3$ | 166 |
| 8d | 2,5-Cl | 140 |
| 9 | 4-F | 130 |

The following compounds of the formula (5) are prepared in a manner analogous to that set forth in Example 2 by reacting the appropriate diphenyldichloromethane from the list on pages 5 to 10 with the appropriate imidazole set forth on page 11.

EXAMPLES 10 – 15

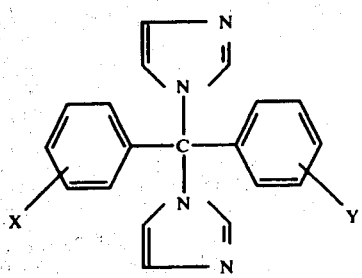

(5)

| | X | Y | m.p. °C |
|---|---|---|---|
| 10 | 2-F | 4-F | 129 |
| 11 | 4-F | 4-F | 196 |
| 12 | 4-F | 4-Cl | 183 |
| 13 | 4-Cl | 4-Cl | 198 |
| 14 | 4-F | 4-$NO_2$ | 198 |
| 15 | 4-F | 4-CN | 190 |

The following compounds of the formula (6) are prepared in a manner analogous to that set forth in Examples 1 and 2 by reacting the appropriate diphenyldichloromethane from the list on pages 5 to 10 with the appropriate imidazole set forth on page 11.

EXAMPLES 16 – 34

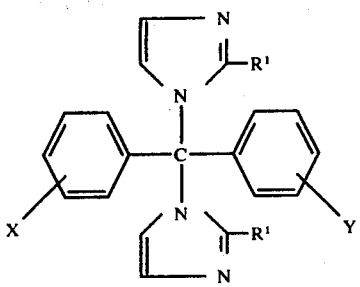

(6)

| | X | Y | $R^1$ | m.p. °C |
|---|---|---|---|---|
| 16 | H | H | $CH_3$ | 193 |
| 17 | 4-F | H | $CH_3$ | 190 |
| 18 | 2-Cl | H | $CH_3$ | 193 |
| 19 | 3-Cl | H | $CH_3$ | 150 |
| 20 | 4-Cl | H | $CH_3$ | 215 |
| 21 | 4-$NO_2$ | H | $CH_3$ | 240 |
| 22 | H | H | $C_2H_5$ | 180 |
| 23 | 4-F | H | $C_2H_5$ | 165 |
| 24 | 4-Cl | H | $C_2H_5$ | 148 |
| 25 | 4-Br | H | $C_2H_5$ | 128 |
| 26 | 2-F | 4-F | $CH_3$ | 250 |
| 27 | 4-F | 4-F | $CH_3$ | 216 |
| 28 | 4-F | 4-Cl | $CH_3$ | 221 |
| 29 | 4-F | 4-$NO_2$ | $CH_3$ | 220 |
| 30 | 4-Cl | 4-Cl | $CH_3$ | 220 |
| 31 | 2-F | 4-F | $C_2H_5$ | 204 |
| 32 | 4-F | 4-Cl | $C_2H_5$ | 174 |
| 33 | 4-F | 4-$NO_2$ | $C_2H_5$ | 197 |
| 34 | 4-Cl | 4-Cl | $C_2H_5$ | 200 |

THERAPEUTIC UTILITY

I. Effectiveness in vitro against human-pathogenic fungi

| 1. | _Trichophyton mentagrophytes:_ | | | |
|---|---|---|---|---|
| | compound a) | < 4 | γ/ml | fungistatic |
| | compound b) | < 4 | γ/ml | |
| | compound c) | < 4 | γ/ml | |
| | compound d) | < 4 | γ/ml | |
| | compound e) | < 4 | γ/ml | |
| | compound f) | < 4 | γ/ml | |
| | compound g) | < 40 | γ/ml | |
| 2. | _Candida albicans:_ | 100 | γ/ml | |
| 3. | _Penicillium com.:_ | 20 | γ/ml | |
| 4. | _Aspergillus niger:_ | 20 | γ/ml | |
| 5. | _Microsp. fel.:_ | 40 | γ/ml | |

The test medium was Milieu d'epreuve according to Sabouraud, incubation temperature: 28° C.

II. In vivo activity:

Taking as example white mice infected i.v. with _Candida albicans_ and _Aspergillus fumigatus_, the new compounds [e.g. (a) to (h)], given orally in doses of 50–100 mg/kg body weight once or twice daily over 5 days, show good curative effects. Dependent upon the dosage, the rate of survival of the animals thus treated amounted to 50 to 85%, of the untreated control animals 0 to 10%.

With the same dosage scheme and a therapy duration of 8 to 10 days, the development of dermatomycoses caused by Trichophyton and Microsporium species can be inhibited in mice and guinea pigs in an average of 70% of the infected animals; in comparison with the untreated-control group, the infection proceeds in the remaining 30% mildly and adheres for only a short period of time.

The local-therapeutic application in the form of ointments and tinctures with a 1% content of active ingredient leads in guinea pigs infected with dermatophytes to healing of the mycosis within 6 to 8 days post infection whereas in untreated control animals the dermatomycosis has an average duration of 28 to 31 days.

Similar results are obtained when, instead of the compounds (a) to (h), the other new compounds or salts are used.

Of special interest for practical use are the compounds which are unsubstituted on the imidazole ring, but which may be substituted in one phenyl moiety by a halogen atom (preferably chlorine, fluorine, in the o-, m- or p-position, i.e. 2-, 3- or 4-position) as well as their salts with hydrochloric acid, lactic acid or salicylic acid.

It is particularly envisaged that the compounds of the present invention may be used in the following manner:
a. in human medicine:
1. Dermatomycoses caused by fungi of the species *Trichophytes, Microporium, Epidermophytes, Aspergillus, Candida albicans*, and other yeasts.
2. Organomycoses caused by yeasts, mould fungi and dermatophytes.
b. in veterinary medicine:
Dermatomycoses and organomycoses caused by yeasts, mould fungi and dermatophytes. The therapeutical application can be effected orally or parenterally as well as locally in the form of solutions (e.g. dimethyl sulphoxide/glycerol/water 2:2:6), alcohol, preferably ethanol and isopropanol, buffer solutions, powders, dreams, ointments and tablets. For topical application preferably a concentration of about from 0.5 to 10% of effective ingredient is used.

For humans the dosage amounts on average to between about 50 and about 100 mg/kg body weight, preferably 50 to about 80 mg/kg body weight, at intervals of up to 12 hours for the duration of about 8 to about 10 days.

However, it may of course be found desirable in some cases to deviate from the quantities indicated here, not only depending on the method of application, but also on possible variations in individual reactions to the compound or the kind of formulation and on the time or the interval at which it is administered. It may thus be possible to manage with less than the abovementioned minimum amount in some cases, whereas in other cases the indicated upper limit may have to be exceeded. If larger quantities are administered, it may be advisable to distribute these in several individual doses over the day.

The compounds of the present invention may be used as such or in combination with pharmaceutically acceptable non-toxic inert diluents or carriers. Suitable forms of application, in combination with various inert carriers, are the following: tablets, capsules, powders, sprays, aqueous suspensions, injectable solutions, elixirs, syrups and the like. Such carriers comprise solid diluents or fillers, a sterile aqueous medium as well as non-toxic organic solvents and the like. Tablets and the like intended for oral use may, of course, be provided with sweetening additives and other conventional substances. The therapeutically active compound should generally be present at a concentration of about 0.5 to 90 per cent by weight of the total mixture, in quantities which are sufficient to achieve the dosage range mentioned above.

For oral application, the tablets can obviously also contain additives, such as sodium citrate, calcium carbonate and dicalcium phosphate together with various other additives, such as starch, preferably potato starch, and the like, and binding agents, such as polyvinyl-pyrrolidone, gelatin and the like. Lubricants, such as magnesium stearate, sodium lauryl sulphate and talc may also be used concurrently for the production of the tablets. In the case of aqueous suspensions and/or elixirs which are intended for oral use, the active substance may be provided with various agents to improve the flavour, colouring substances, emulsifiers and/or with diluents, such as water, ethanol, propylene glycol, glycerol and similar compounds or combinations.

For parenteral application, solutions of the active substances in sesame or peanut oil, or in aqueous propylene glycol or N,N-dimethyl formamide can be employed as well as sterile aqueous solutions in the case of water-soluble compounds. Aqueous solutions of this kind should be buffered in the usual manner if necessary; furthermore, the liquid diluent should be rendered isotonic from the start by the addition of the necessary amount of salt or glucose. Such aqueous solutions are particularly suitable for intravenous, intramuscular and intraperitoneal injections.

Sterile aqueous media of this kind are prepared in known manner.

In mice, rats, rabbits, dogs and cats the $LD_{50}$ of the compounds mentioned above ranges from about 500 and 1000 mg/kg body weight when orally administered.

The present invention also includes pharmaceutical compositions comprising one or more compounds as hereinbefore described as the active ingredient in combination with a pharmaceutically acceptable non-toxic inert diluent or carrier.

The present invention further provides a medicament in unit dosage form which comprises at least one of the compounds hereinbefore described either alone or in combination with a pharmaceutically acceptable inert diluent or carrier. The medicament may include a protective envelope containing the active compound and if used the diluent or carrier.

The term "medicament in dosage unit form" as used in the present specification means a medicament as defined above in the form of discrete portions each containing a unit dose, or a multiple or sub-multiple of a unit dose of the active compound or compounds. Such portions may, for example, be in monolithic coherent form, such as tablets, suppositories, pills or dragees; in wrapped or concealed form, such as wrapped powders, cachets, sachets, or capsules; in ampoules, either free or as a sterile solution suitable for parenteral injection; or in any other form known to the art.

Besides the antimycotic activity the compounds show an activity against pathogenic protozoa, e.g. Trypanosoma, Trichomonas, Entamoeba histolytica, malaria parasites, Toxoplasma and against viruses and bacteria, e.g. Staphylocci, Streptococci, Klebsiella, E. coli.

Further the compounds activate the granulation in wound healing and show a hypocholesterinaemic activity.

What is claimed is:
1. A compound of the formula:

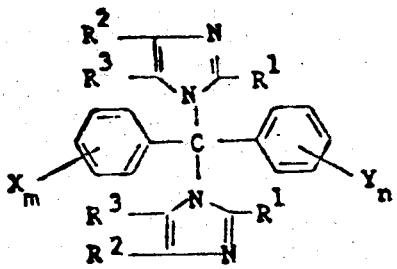

wherein
R¹ is hydrogen, alkyl of 1 to 4 carbon atoms or phenyl,
R² and R³ are the same or different and are hydrogen, alkyl of 1 to 4 carbon atoms or phenyl,
X and Y are the same or different and are halogen, NO$_2$, CN, alkyl of 1 to 12 carbon atoms, S-alkyl of 1 to 4 carbon atoms or alkoxy of 1 to 4 carbon atoms, and
m is 0, 1 or 2, and
n is 1 or 2 or m is 1 or 2 and n is 0, 1 or 2.

2. A compound according to claim 1 wherein R¹ is hydrogen or alkyl of 1 to 4 carbon atoms, R² and R³ are hydrogen, X and Y are the same or different and are halogen, CN, NO$_2$, methoxy or methyl and n is 0 or 1.

3. A compound of the formula

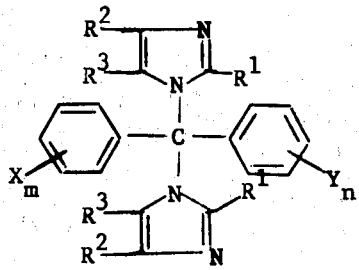

wherein R¹, R² and R³ are hydrogen, X and Y are the same or different and are fluorine, chlorine, bromine, iodine, CN, NO$_2$, methoxy, or thiomethyl and m and n are 1.

4. A compound of the formula

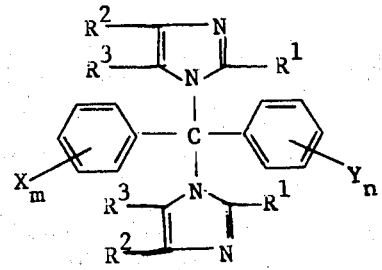

wherein R¹, R² and R³ are hydrogen, and one of X and Y is halogen in the 2-, 3- or 4-position.

5. The compound bis-imidazolyl-4-chlorophenyl-phenylmethane.
6. The compound bis-imidazolyl-4-fluorophenyl-phenylmethane.
7. The compound bis-imidazolyl-2,4'-difluoro-diphenylmethane.
8. The compound bis-imidazolyl-2-chlorophenyl-phenylmethane.
9. The compound bis-imidazolyl-3-chlorophenyl-phenylmethane.
10. The compound bis-imidazolyl-4-cyanophenyl-phenylmethane.
11. The compound bis-(2-methylimidazolyl)-4-chlorophenyl-phenylmethane.

* * * * *

UNITED STATES PATENT AND TRADEMARK OFFICE
CERTIFICATE OF CORRECTION

PATENT NO. : 3,985,766
DATED : October 12, 1976
INVENTOR(S) : Erik Regel, Karl Heinz Buchel and Manfred Plempel It is certified that error appears in the above-identified patent and that said Letters Patent are hereby corrected as shown below:

In column 12, line 23, after "position", insert -- and the other is $NO_2$, CN, alkyl of 1 to 12 carbon atoms, S-alkyl of 1 to 4 carbon atoms or alkoxy of 1 to 4 carbon atoms, and
$\underline{m}$ is 0, 1 or 2, and
$\underline{n}$ is 1 or 2
or $\underline{m}$ is 1 or 2 and
$\underline{n}$ is 0, 1 or 2 --

Signed and Sealed this

Eighth Day of February 1977

[SEAL]

Attest:

RUTH C. MASON
*Attesting Officer*

C. MARSHALL DANN
*Commissioner of Patents and Trademarks*